United States Patent [19]
Bruchman et al.

[11] Patent Number: 4,776,851
[45] Date of Patent: Oct. 11, 1988

[54] MECHANICAL LIGAMENT

[76] Inventors: William C. Bruchman, 160 E. Appalachian Rd., Flagstaff, Ariz. 86001; Scott N. Stonebrook, Box 883, Parks, Ariz. 86018

[21] Appl. No.: 888,216
[22] Filed: Jul. 23, 1986
[51] Int. Cl.⁴ .............................................. A61P 2/08
[52] U.S. Cl. ................................................. 623/13
[58] Field of Search ............................ 623/13; 403/43
[56] References Cited

U.S. PATENT DOCUMENTS

| 2,403,828 | 11/1943 | Rawlins et al. | 403/43 |
| 3,513,484 | 11/1987 | Hausner | 623/13 |
| 3,953,896 | 5/1976 | Treace | 623/13 |
| 3,988,783 | 11/1976 | Treace | |
| 4,136,405 | 1/1979 | Pastrick et al. | |
| 4,149,277 | 4/1979 | Bokros | 623/13 |
| 4,246,660 | 1/1981 | Wevers | 623/13 |
| 4,538,305 | 9/1985 | Engelbrecht et al. | |
| 4,578,080 | 3/1986 | Helal | 623/13 |

OTHER PUBLICATIONS

Clinical Orthopaedics; C. W. Bolton et al; vol. 186:202 (1985), Gore-Tex TM Expanded PTFE Prosthetic Ligament.

Primary Examiner—Richard J. Apley
Assistant Examiner—James Prizant
Attorney, Agent, or Firm—Dena Meyer

[57] ABSTRACT

The present invention relates to a prosthetic ligament comprising at least one intra-osseous bearing members in a bone of a joint and an intra-articular linkage means connecting the intra-osseous member to the other bone so that multiple degrees of motion are provided between the bones.

7 Claims, 5 Drawing Sheets

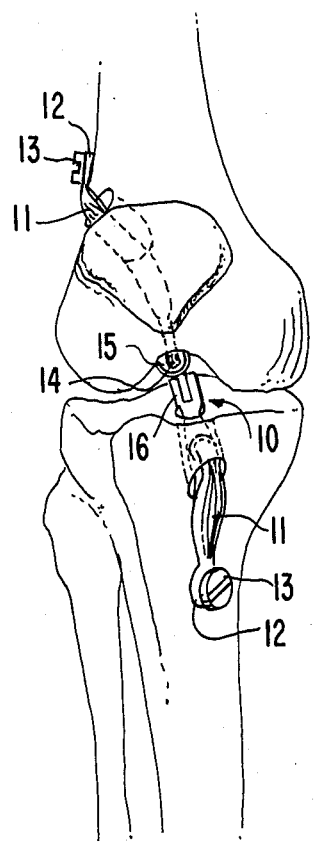
FIG. 1.
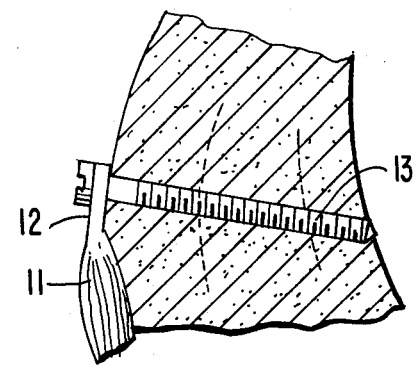
FIG. 1a.
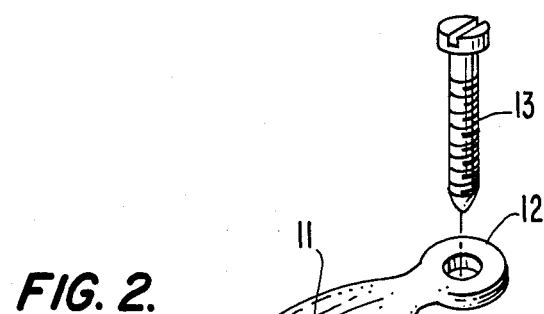
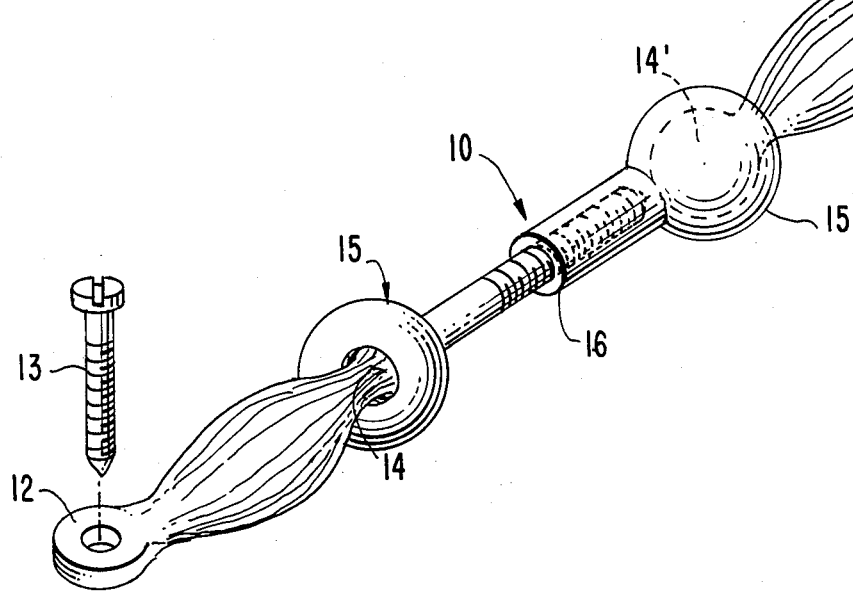
FIG. 2.

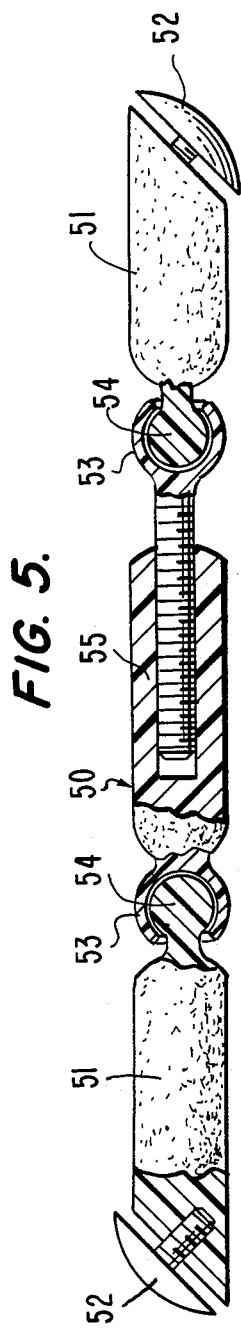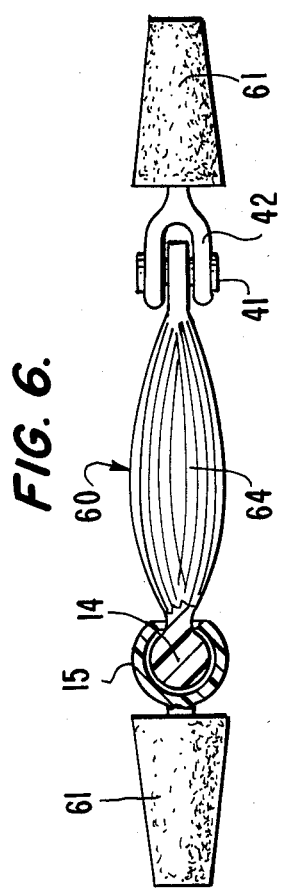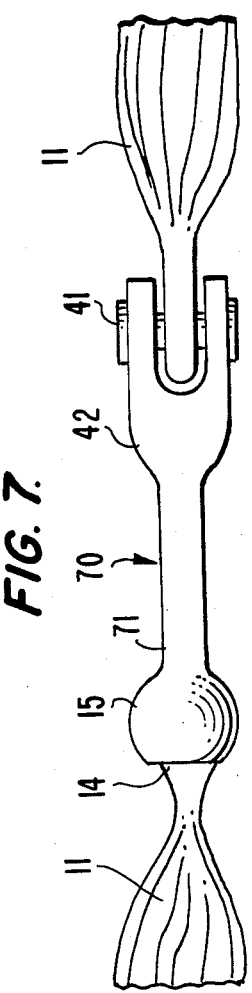

MECHANICAL LIGAMENT

BACKGROUND OF THE INVENTION

This invention relates to a mechanical prosthesis for replacement of a ligament between two bones in the human body. Within the context of this invention, ligaments are defined as bands of fibrous tissue connecting articulated bones.

The primary function of these ligaments is to provide restraints to the movement of one bone relative to another. During body movement, tensile loads are imposed on the ligaments. The rotation of one bone relative to another that occurs with this articulation also causes bending in the ligaments. The loss of or damage to these ligaments leads to abnormal joint movement and disability.

Current ligament prostheses attempt to mimic the natural ligament through the use of flexible materials. These materials possess different physical properties than the natural ligament. Failure in these prostheses has often been due to inadequate tensile strength or loss of tensile strength with time. Even if the initial strength of the material is adequate, the physical geometry of the prosthesis dictated by attachment to bone and by joint flexion may lead to failure through fatigue, abrasion, and cutting against bone surfaces.

Previous authors have taught the use of prosthetic joints with bearing surfaces to replace a natural joint in the body. Unlike these prior references, the present invention involves the use of mechanical elements, that is, a combination of links and bearings to preserve the joint and restore normal movement.

SUMMARY OF THE INVENTION

A prosthesis to replace a ligament connecting two adjacent bones of the body is provided comprising at least one bearing member affixed to one bone, and linkage means connecting the bearing member to the other adjacent bone, whereby the linkage means and bearing member provide multidimensional freedom of movement between the two adjacent bones. The linkage means may include a second bearing affixed to the other bone. The bearing member may be a ball and socket or a hinge. The linkage means may be a chain, a turnbuckle, a rigid linkage means, or strands of a synthetic polymer in a braided, woven or multistranded form. In one embodiment, the prosthesis has two bearing members which are balls and sockets and turnbuckle linkage means. In another embodiment, the prosthesis has one bearing member which is a ball and socket, the linkage means is a turnbuckle and the second bearing is a clevistype hinge. The synthetic polymer is preferably expanded, porous polytetrafluoroethylene.

BRIEF DESCRIPTION OF THE DRAWINGS

FIG. 1 depicts schematically one embodiment according to the invention implanted in a knee joint.

FIG. 1a depicts schematically the attachment of the prosthesis to a bone.

FIG. 2 shows a schematic perspective view of one prosthesis constructed in accordance with the present invention.

FIG. 5 shows a schematic perspective of yet another prosthesis constructed in accordance with the present invention.

FIG. 6 shows a schematic perspective view of another prosthesis constructed in accordance with the present invention.

FIGS. 7, 8, 9 and 10 show schematic perspective views of the prosthesis with rigid linkage constructed in accordance with the present invention.

DETAILED DESCRIPTION OF THE PREFERRED EMBODIMENTS

Figure 2A:
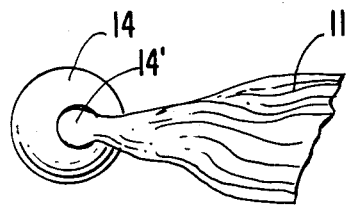
FIG. 2a shows schematically the bearing portion of the prosthesis with the porous polymer strands compressed and shaped into a ball.

The present invention relates to a prosthetic ligament wherein there is at least one intra-osseous bearing member in a bone of a joint and an intra-articular linkage means connecting the intra-osseous member to the other bone so that multiple degrees of movement are provided between the bones. The intra-osseous bearing member is built to fit snugly into a surgically prepared bone tunnel that exits near the attachment of the ligament to be replaced. One end of the linkage member is connected to the bearing member and the other end of the linkage member is attached to a second intra-osseous member implanted into the other bone or connected directly to the other bone. The prosthesis may be implanted completely assembled and adjusted during surgery or may be assembled, implanted and adjusted during surgery.

According to the present invention, the flexible collagenous structures comprising natural ligaments which connect bones in a joint are replaced by a combination of mechanical elements which allow multidimensional bone movement. Bearings are provided in strategic positions of the prosthesis to provide for rotational movement about one or more axes. Linkage means may be either rigid or flexible and may connect the bearings to one another and to the bones. The use of bearings eliminates fatigue considerations arising from joint motion. The invention provides for use of rigid metallic materials or composite materials that are resistant to abrasion or erosion by bone surfaces. The problem of reduced effective lifetime of synthetic ligaments due to abrasion is thus substantially eliminated.

FIGS. 1 and 1a depict schematically one embodiment of a three-membered prosthesis according to the invention. The prosthesis 10 is shown in detail in FIG. 2. The intra-osseous members 11 contain the bearing members and may be constructed of a multistranded, strong, porous polymer such as expanded, porous polytetrafluoroethylene that allows for tissue ingrowth. One end of each member 11 is formed into an eyelet 12. Each eyelet may then accept a cortical bone screw 13 as shown in FIG. 1a for fixation to a bone outside the joint.

As shown in FIG. 2, the intra-articular connecting linkage means 16 comprises a turnbuckle with sockets 15 on either end that receive the ball portions 14 of the intra-osseous members. The ball and socket hinges and turnbuckle allow for movement both radially and vertically. The turnbuckle allows for adjustment of the length of the prosthesis during surgery.

Figure 2B:
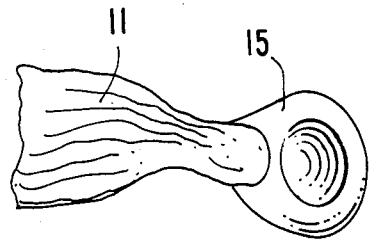
FIG. 2b shows schematically the bearing portion of the prosthesis wherein a metal socket is attached to the end of the intra-osseous member.

FIGS. 2a and 2b show two different embodiments of the bearing portion 14 of the intra-osseous members 11. In FIG. 2a, the strong, porous polymer strands are compressed and shaped into a small ball 14. This small ball is further surrounded by a heat treated hard thermoplastic such as polyethylene and further shaped into a ball 14.

FIG. 2b shows an alternative embodiment wherein a metal socket is attached to the end of the intra-osseous member. The socket may be either a one or two piece member and is capable of holding the compressed end of the intra-osseous member by either a pin or a set screw passing through the compressed end.

Figure 3:
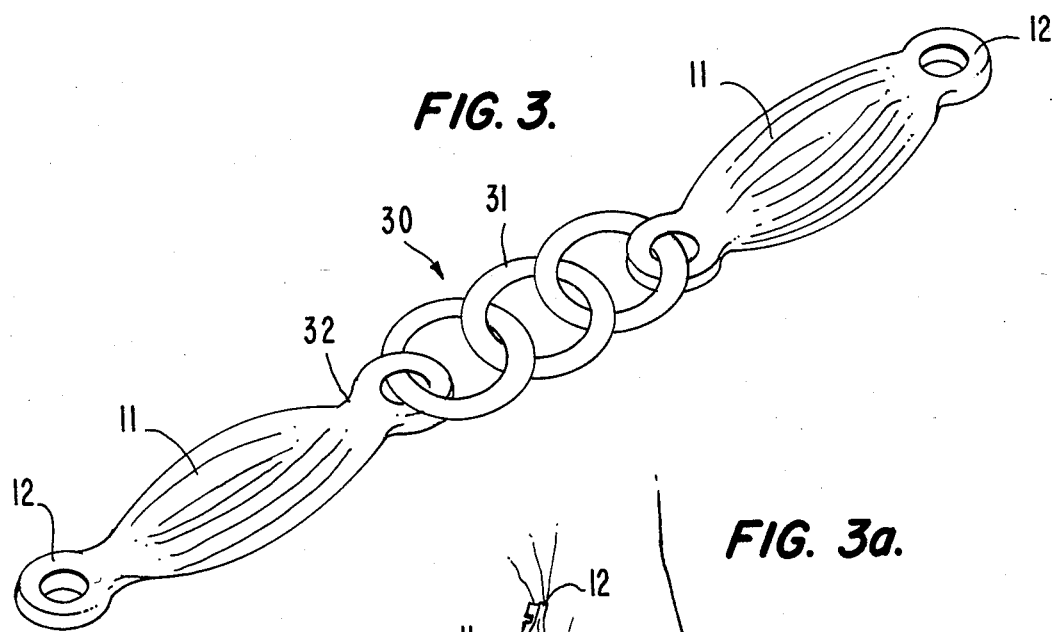
FIG. 3 shows a schematic perspective view of another prosthesis with chain linkage constructed in accordance with the present invention.
Figure 3A:
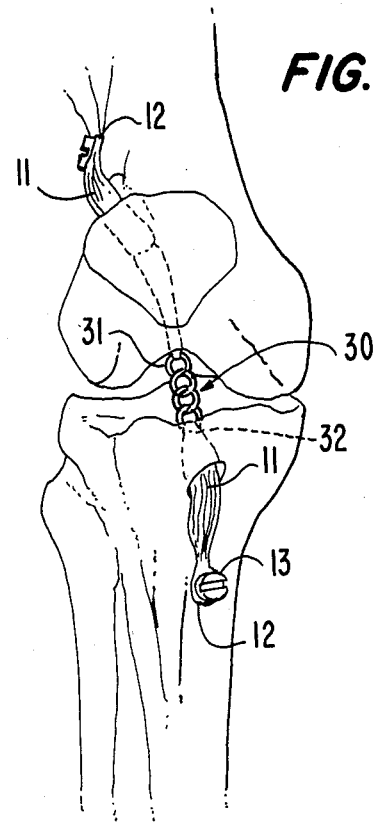
FIG. 3a shows schematically the prosthesis with chain linkage implanted in a knee joint.
Figure 4:
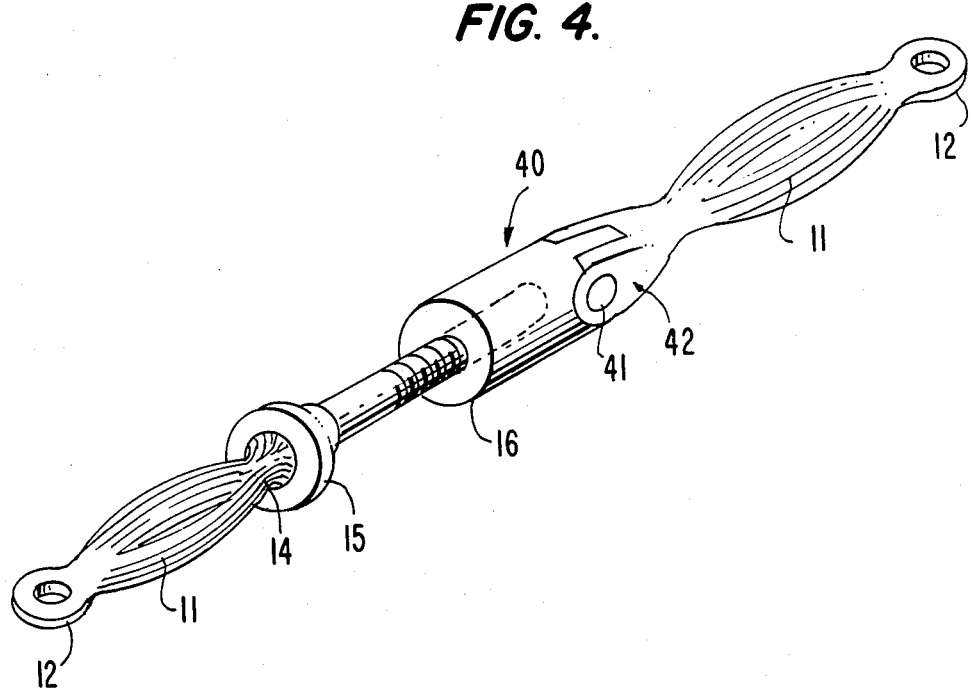
FIG. 4 shows a schematic perspective view of another prosthesis with turnbuckle linkage constructed in accordance with the present invention.

FIGS. 3, 3a and 4 show further embodiments of the invention. In FIG. 3, the intra-osseous members 11 are similar to those of prosthesis 10 in FIG. 2, however, the ends of these members are compressed and formed into a loop 32 to be connected by means of a chain linkage 31. This prosthesis is attached to the bone joint in a manner similar to that discussed above as shown in FIG. 3a. Eyelets 12 are formed at the outer ends of the intra-osseous members 11 and accept a cortical bone screw 13 for fixation outside the joint. The linkage means 31 is a chain and may be comprised of a biocompatible metal such as titanium or polymer such as expanded polytetrafluoroethylene. The linkage means allows for adjustment of the length of the prosthesis during surgery. This embodiment allows for rotational movement as well as movement in horizontal and vertical directions.

In FIG. 4, the linkage means 16 is a turnbuckle. The bearing means comprises a socket 15 located on one end of the linkage means to receive a ball 14 similar to that described above. The second bearing means comprises a clevis hinge 42 on the other end of the turnbuckle that is adapted to fit onto an intra-osseous member 11. The clevis hinge 42 is to be constructed of a biocompatible metal which fits snugly within a compressed portion of the expanded, porous polytetrafluoroethylene polymer used in the intra-osseous member 11 and is held in place by a screw 41. The intra-osseous member containing the ball on one end is similar to that described above. The method of implanting and attaching prosthesis 40 to the bone joint is similar to that described above. This configuration also provides bone movement both radially and vertically.

Figure 5A:
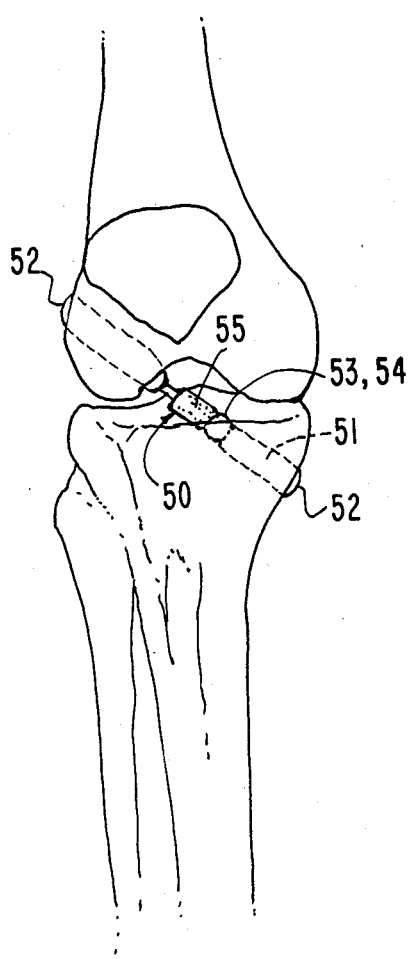
FIG. 5a depicts schematically another means of implanting the prosthesis in a knee joint.

FIG. 5 shows another embodiment of the invention. FIG. 5a shows the prosthesis 50 implanted in a knee joint. Referring to FIG. 5a, intra-osseous bearing members 51 are constructed of titanium or other biocompatible metal and are press fit into the bone tunnels. Screws 52 are provided for immediate external fixation of the prosthesis to the bones. The other ends of the intra-osseous members are shaped into balls 54 which are received by the sockets 53 which are located at each end of the intra-articular linkage means 55. In this illustration, the intra-articular connecting means 55 is a turnbuckle. Alternatively, the intra-osseous means may have sockets fitted at the ends adjacent to the linkage means. The linkage means may have both ends shaped into balls which may be received by the sockets.

Figure 6A:
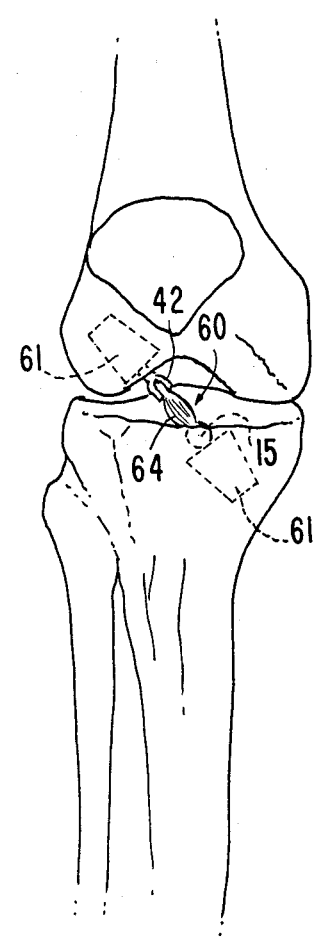
FIG. 6a depicts schematically the prosthesis of FIG. 6 implanted in a knee joint.

FIG. 6 shows another embodiment 60 of the invention. Here the intra-osseous bearing members 61 are frusto-conical shaped and constructed of a biocompatible metal. The intra-osseous members are press fit into the bone tunnel. For this embodiment, it is not necessary to provide for external fixation to the bone.

In this embodiment, one of the intra-osseous members is fitted with a socket 15. The other intra-osseous member is fitted with a hinge 42. The intra-articular linkage means 64 is a polymeric material, preferably expanded polytetrafluoroethylene, which is compressed into a ball 14 at one end and is compressed at the other end to form an eyelet 65. The central region of the connecting member 64 may be braided, woven, or multistranded. The ball 14 is received in the socket 15 of one intra-osseous member and the eyelet 65 fits within the hinge 42 of the other intra-osseous member. This configuration also provides for bone movement in rotational, horizontal and vertical directions.

Figure 8:
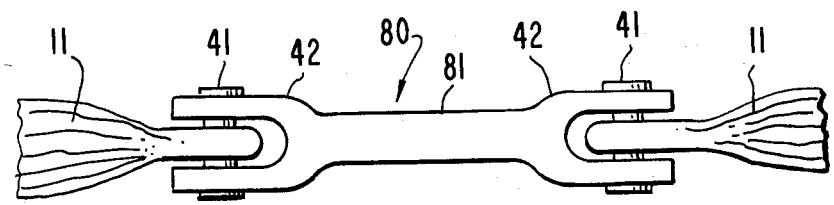
Figure 9:
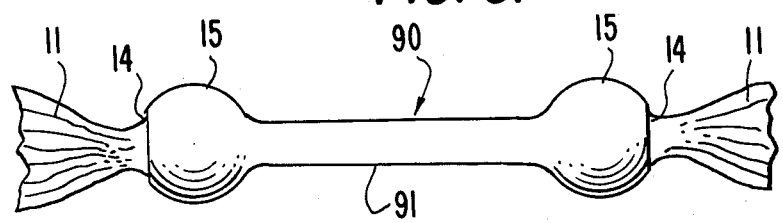

FIGS. 7 through 10 show embodiments in which the linkage means comprises a rigid bar. In FIGS. 7, 8 and 9, the intra-osseous bearing members consist of multistranded, porous polymers that have a loop at the outer end for bone attachment by a cortical screw. In FIG. 7, one end of the first intra-osseous bearing member is adapted for a ball and socket bearing. The intra-articular linkage means is comprised of a rigid bar and the second intra-osseous bearing member is fitted for a clevis hinge. The intra-articular linkage means may be constructed of a biocompatible metal. This configuration provides for rotational movement as well as movement in the vertical and horizontal direction.

FIG. 8 is constructed in a manner similar to that of FIG. 7 except that both bearing members are clevis hinges. This configuration provides for rotational movement as well as movement in the vertical and horizontal direction.

Figure 10:
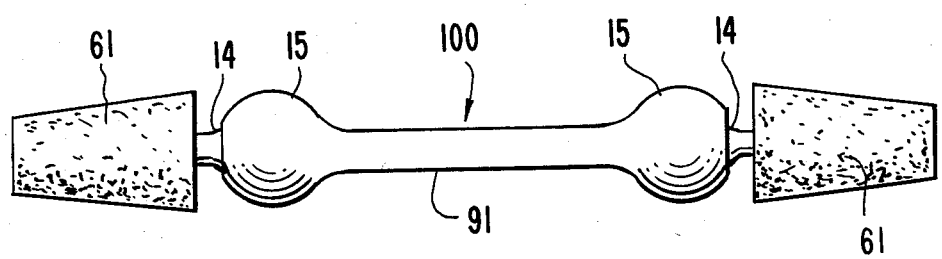

FIGS. 9 and 10 depict mechanical ligaments in which the bearing members are balls and sockets and the linkage means is a rigid bar. FIG. 9 shows an intra-osseous member comprised of multistranded porous polymer. The ligament shown in FIG. 9 permits for rotational movement as well as movement in the vertical and horizontal directions.

FIG. 10 shows an embodiment in which the intra-osseous members are frusto-conical and are constructed of a biocompatible metal. Here, as described above, the intra-osseous members are press fit into the bone tunnel. This configuration provides for rotational movements as well as movement in the vertical direction.

It is to be understood that the foregoing description and the accompanying drawings are illustrative of the invention and are not to be taken as limiting the scope of the appended claims.

We claim:

1. A prosthetic ligament for connecting two adjacent bones of the body, said ligament comprising:
    (a) an intra-osseous member to be affixed at one end thereof to one of said bones, the intra-osseous member having a bearing member affixed at the other end thereof, said bearing member having at least one-dimensional freedom of movement;
    (b) linkage means connected to said bearing member and having means for connecting said linkage means to said other adjacent bone, said linkage means having at least one-dimensional freedom of movement, (c) said bearing member being selected from the group consisting of ball and socket, hinge, and clevis-type hinge bearings;

whereby, said linkage means and bearing member provide multi-dimensional freedom of movement between said two adjacent bones when connected by said prosthetic ligament.

2. The prosthesis of claim 1 wherein said linkage means is a chain.

3. The prosthesis of claim 1 wherein there is second bearing comprising a ball and socket affixed to said linkage means and said other bone.

4. The prosthesis of claim 3 wherein said bearing members are clevis hinges and socket bearing members and said linkage means is a turnbuckle.

5. The prosthesis of claim 3 wherein one bearing member is a ball and socket, said linkage means in a turnbuckle and said second bearing is a clevis.

6. The prosthesis of claim 3 wherein said bearing members are balls and sockets and said linkage means is a rigid bar.

7. The prosthesis of claim 3 wherein one said bearing member is a ball and socket and the other is a clevis hinge in place of said ball and socket and said linkage means is a rigid bar.

* * * * *